United States Patent [19]

Moore

[11] Patent Number: Plant 5,330

[45] Date of Patent: Nov. 13, 1984

[54] MINIATURE ROSE PLANT

[75] Inventor: Ralph S. Moore, Visalia, Calif.

[73] Assignee: Sequoia Nursery, Visalia, Calif.

[21] Appl. No.: 461,986

[22] Filed: Mar. 14, 1983

[51] Int. Cl.[3] ..... A01H 5/00

[52] U.S. Cl. ..... Plt./9

[58] Field of Search ..... Plt./9

*Primary Examiner*—Robert E. Bagwill

[57] ABSTRACT

This invention relates to a new and distinct variety of miniature rose plant primarily identified by its coral pink buds and flowers.

1 Drawing Figure

1

The present invention relates to a new and distinct variety of hardy, dwarf, bush type rose plant of the miniature class; the variety being primarily characterized — as to novelty — by the coral pink buds and flowers which generally are of exhibition (Hybrid Tea) form.

The variety is further characterized by:

An abundance of bloom, with flowers usualy borne singly, but also several to the stem in loose clusters.

Some fragrance.

A plant which is vigorous, of rounded, upright shape with small semi-glossy to matt foliage with pointed leaflets; the buds and flowers being similar in form and size to Sheri Anne (miniature — U.S. Plant Pat. No. 3,826) — but with more petals.

The plant, which has a normal height of 14–18 inches or more, can easily be maintained at lesser height by occasional trimming.

A plant which grows and blooms satisfactorily both in greenhouse and outdoors; is good for growing in pots; and provides excellent garden decoration was well as cut flowers.

The present variety of miniature rose was originated by me at Sequoia Nursery located at Visalia, Calif., under conditions of careful control and observation, as a cross between Little Darling (U.S. Plant Pat. No. 1,581 — expired — floribunda) as the seed parent and Anytime (miniature — not patented) as the pollen parent.

Subsequent to origination of the variety I successfully asexually reproduced it at Sequoia Nursery, located as aforesaid, by budding as well as by cuttings; the reproductions having run true in all respects.

The color photograph illustrates the variety, including the foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bushy; upright; seedling; greenhouse; outdoors; cut flowers; garden decoration; potted plant.

Class: Miniature. Variety identification: MORcalyn (Commercial synonym: Coral Cameo).

Flowers borne: Singly and several together (3 to 5 ) on slender wirey stems.

Quantity of bloom: Abundant both outside and in greenhouse.

2

Bud:

*Peduncle.*—Medium length; slender but sturdy; erect; medium to light green, sometimes tinted bronze (outdoors); with no prickles and numerous very short hairs.

*Before calyx breaks.*—Size — small. Form long; pointed with few or no foliaceous apendages on surface of bud; with foliaceous parts extending beyond the tip of the bud equal to one-half or less of its length. Color — medium green, occasionally tinted with bronze (outdoors).

*As calyx breaks.*—Color — light pink, often greenish at base. Opening: opens well in all weather.

Bloom:

*Size when fully open.*—Small, averaging about 35 mm (1½").

*Petalage.*—Double — averaging about 40 petals, arranged regularly plus several small petaloids.

*Form.*—High centered with petals rolled loosely outward and downward. Open flowers may show stamens.

Petals: Fairly thick; satiny on inside and on outside surface.

*Shape.*—Outside petals, broad lanceolate (nearly round) with small acute tip; intermediate — broad lanceolate with small acute tip; inside — lanceolate with acute tip.

Color: (Newly opened flower from a plant grown in plastic greenhouse (November 1982), Visalia, Calif.):

*Outside petal.*—Outside surface — soft pink, near Carmine Rose 621/3 (or lighter), becoming yellowish to greenish at base. Inside surface — near Carmine Rose 621/3 becoming slightly lighter shade of pink on basal half of petal, with small yellow area at base.

*Intermediate petal.*—Outside surface — similar to outside petal. Inside surface — similar to outside petal but usually deeper shade. As flower opens color lightens, becoming similar to outside petal surface.

*Inner petal.*—Outside surface — same as intermediate petal; inside surface — same as intermediate petal. General color effect; buds and newly opened flowers — soft blend of pink shades with lighter reverse. Three days open — open-color — similar to newly opened flowers, but lighter color — then aging to darker pink at petal tips. Behavior — opens well in all weather. Spent petals drop off. Flower longevity (October 1982) — plant in pot 4–6 days or longer. Cut flowers at living room temperature 4–5 days or longer.

Reproductive organs:

*Stamens.*—Arranged regularly about pistils.

*Filaments.*—Varying length, medium long, yellow.

*Anthers.*—Well formed; yellow.

*Pollen.*—Small amount.

*Pistils.*—Average number.

*Styles.*—Varying length — quite long; greenish; bunched; often malformed.

*Ovaries.*—All enclosed in calyx.

*Hips.*—None.

*Sepals.*—Permanent; spear shaped; recurved.

*Seed.*—None.

Foliage:

*Leaves.*—Compound of five (sometimes three or seven) leaflets; medium small; leathery; semi-glossy to matt.

*Leaflets.*—Shape: broad, nearly oval; apex acute; base rounded — sometimes acute.

*Color.*—Medium green; new growth — normal (medium) green (sometimes tinted reddish).

*Rachis.*—Medium strength; upper side may have few or no prickles or hairs; grooved; underside may have several thorns (1 to 3) and few or no tiny prickles or hairs.

*Stipules.*—Medium to short length; medium width; short to medium length narrow points which turn out usually at about 45 degrees or more.

Growth:

*Habit.*—Dwarf; bushy; upright; much branched.

*Growth.*—Free; vigorous; internodes short.

*Canes.*—Medium; slender; sturdy.

*Main stems.*—Color: medium green. Thorns: several. Prickles — none. Hairs — none.

*Branches.*—Color: medium green. Thorns; several; slender. Prickles: none. Hairs — none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, bushy, upright, much branched habit, substantially as illustrated and described, characterized by buds and flowers of exhibition form, essentially light pink in color, the petals being a blend of pink shades and changing to darker pink at petal tips in more mature stage, and further characterized by a plant of compact well rounded shape, vigorous, with the main stems and shoots being moderately thorny, the said plant being easy to propagate from cuttings or by budding, with an abundance of small semi-glossy to matt foliage and an abundance of flowers borne singly or several to the stem in loose clusters.

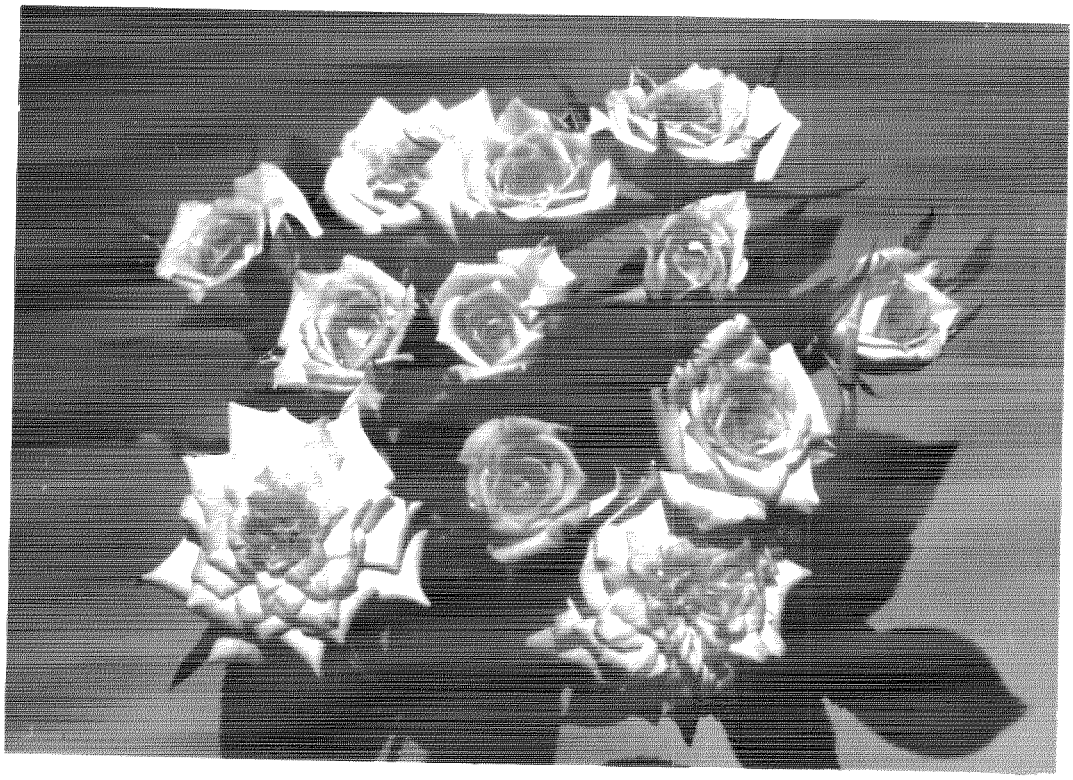

* * * * *